United States Patent [19]

Dobritz

[11] 4,010,748
[45] Mar. 8, 1977

[54] BREATHING AIR HUMIDIFIER FOR RESPIRATION DEVICES

[75] Inventor: Günter Dobritz, Lubeck, Germany

[73] Assignee: Dragerwerk Aktiengesellschaft, Germany

[22] Filed: June 26, 1975

[21] Appl. No.: 590,632

[30] Foreign Application Priority Data

June 27, 1975  Germany ............ 2430875

[52] U.S. Cl. .................. 128/192; 128/186; 128/145.5; 261/36 R; 261/DIG. 65
[51] Int. Cl.² .......................... A61M 16/00
[58] Field of Search .............. 128/186–188, 128/192, 212; 261/36 R, 104, 101, DIG. 65

[56] References Cited

UNITED STATES PATENTS

| 3,520,416 | 7/1970 | Keedwell | 261/104 |
| 3,587,573 | 6/1971 | Flack | 128/208 |
| 3,871,373 | 3/1975 | Jackson | 128/212 |
| 3,912,795 | 10/1975 | Jackson | 261/36 R |

Primary Examiner—Robert W. Michell
Assistant Examiner—Henry J. Recla
Attorney, Agent, or Firm—McGlew and Tuttle

[57] ABSTRACT

A breathing air humidifier for respirator devices comprising an inspiration conduit which is connected to the mouth of the user of the respirator and which has a section or portion with a foil surface of a material which is impervious to water but pervious to water vapor. A water chamber surrounds the foil surface and water which is warmed is delivered to the water chamber from a supply tank located above the chamber which carries a heater for warming the water to a preselected temperature.

10 Claims, 3 Drawing Figures

BREATHING AIR HUMIDIFIER FOR RESPIRATION DEVICES

BACKGROUND OF THE INVENTION

1. Field of the Invention

This invention relates in general to the construction of a breathing air humidifier for respirators and in particular to a humidifier which includes an inspiration conduit which has a foil surface of a material which is impervious to water but pervious to water vapor and which is in communication on its interior with the air being inspirated and on its exterior with heated water.

2. Description of the Prior Art

In an artificial respiration of patients by means of intubation and also during the spontaneous breathing a tracheotomized patient, the breathing air no longer passes through the laryngeal, nasal and pharyngeal cavities but passes directly into the bronchi. Since the laryngeal, nasal and pharyngeal cavities are no longer contacted by the breathing air this air can no longer be sufficiently warmed and humidified. The result is the drying up of the breathing air ways and the endangering of the function of the vibrating epithelium. In order to prevent the drying up of the breathing air ways or passages it is well known to provide breathing air humidifiers. The function of such a humidifier is to warm the inspiration air preferably up to the body temperature and at the same time to bring it to a relative humidity as high as possible preferably 100%. Almost all of the known breathing air humidifiers have the substantial drawback that the water evaporating therein increases the vacuum volume at the inspiration side. Due to the unavoidable impression under the inspiration pressure which may amount to 120 mm of water column, the inspiration volume difference between the respiration with and without water in the humidifier may amount to 20%. This for example in the respiration of infants is a very critical percentage difference.

Many types of breathing air humidifiers are known in the prior art:

With the so-called bubbler type the inspiration air is conducted through warmed water which humidifies the air. Entrained water droplets are retained by a granular matter provided above the water surface. The disadvantage of such bubblers is that the compressible volume varies with the volume of the water which is filled in. In addition the device is so bulky that it cannot be placed directly adjacent the patient's mouth. In long supply lines however the air tends to cool down. Consequently, a portion of the humidity contained in the inspiration air will condense. This condensate must be kept away from the patient by appropriate measures.

Humidifiers comprising a wick operated in a similar manner as the bubblers and as a surface humidifier has the disadvantage that the wick does not bring the air so intimately into contact with the water. The air flows past moistened wicks which take warmed water from a reservoir. Such humidifiers have the same drawbacks as the bubblers. However because they can be of smaller design it is possible to place them closer to the patient. The problems of condensation are therefore relatively more favorable but on the other hand it is more difficult to obtain a satisfactory humidification of the breathing air. Another air humidifier uses a hot vapor injection into the inspiration air stream. To produce the hot vapor the humidifier comprises a heated plate on which an adjustable quantity of water is evaporated. The water vapor which is produced passes into the inspiration air system and humidifies and warms the air. Air humidifiers of this kind can be constructed in a very small size. Thus condensation is no problem. The adjustment of the correct quantity of water for humidification of the air is very difficult. To small breathing air volumes may become overheated and too large a breathing air volume per minute may lead to an insufficient humidification and to a low temperature.

SUMMARY OF THE INVENTION

In accordance with the present invention there is provided a breathing air humidifier in which the compressible volume remains constant independently of the water consumption and which can be designed so small that in order to avoid condensation it can be mounted directly into the inspiration air supply close to the patient. In accordance with the invention the evaporation surface is formed by a surface of a foil which is impervious to water but which is pervious to water vapor. Warm water is brought into contact with one side of the foil while the gas to be humidified that is the inspiration passage is conducted past the other side of the foil. With such an arrangement the physical process in the laryngeal, nasal and pharyngeal cavities is reproduced. Through a large surface area, the evaporated water enters the inspiration air stream which flows past. At the same time the stream is warmed up to the water temperature. The amount of heat necessary for the evaporation and for the warming up of the breathing air can usually be taken from the water. It is advantageous that the water quantity necessary for humidifying the inspiration air is removed from the water without changing the compressible vacuum volume.

According to a development of the invention the foil is made either by macroporous material which is made of a hydrophobic or it may be made of a microporous hydrophilic material. Either of such foil materials may be used to separate the water from the inspiration air stream to be enriched with the water vapor. The warm water contacts one side of the foil but it does not pass through the foil. Only evaporated water in the form of water vapor passes therethrough into the stream of inspiration air flowing past the other side of the foil and it thereby increases its humidity. The vacuum volume remains unchanged. At the water contacted side of the foil the evaporated water is continuously replaced by a further supply of warm water.

According to a further development of the invention the evaporation surface is located in a receptable in which the foil is contacted on one side by water and on the other side by the gas to be humidified and the space of the water contacted side constitutes the flow return area of a thermostatically heated warm water circuit in which the water circulates from and into a supply tank. The gas contacted side is connected into the inspiration air conduit through which the inspiration air stream is directed to the patient's mouth. The warm water circuit may comprise a water pump but the circulation of the warm water may also be effected by means of a heat source provided in the water return conduit. Due to such an arrangement the breathing air humidifier and the necessary water supply conduit can be disposed at separate locations. The breathing air humidifier may be placed very close to the patient's mouth. This makes the inspiration air conduit downstream of the air humidifier very short so that there is little danger of a rapid cooling of the inspirated air with a resultant undesirable condensation.

In order to insure a reliable operation of the respiration device, it is advantageous to dispose the supply tank so as to obtain a water pressure on the evaporating surface which is greater than the maximum pressure in the inspiration air stream. This makes sure that during the entire inspiration period the water is fully and permanently applied against the evaporation surface and the evaporation is optimal.

In order to save space two mutually coupled check valves may be provided instead of using static water pressure and these check valves are controlled by the pressure in the inspiration air stream and they are adapted to interrupt the water circulation in both the water return conduit and the water supply conduit which leads to the breathing air humidifier.

In order to obtain an evaporation capacity as large as possible the foil surface is advantageously made of a star shaped configuration to offer as large an area of foil surface as possible. In this case the water contacted side is turned to the inside surface of the receptacle. In order to further improve the operation turbulence producing means may be provided at the gas contacted side of the evaporation surface. Thereby the humid boundary layers are engaged by the inspiration air stream in a still more satisfactory manner.

In order to further increase the security a foil made of the same material as the evaporation surface and extending across the inspiration air conduit may be provided downstream of the evaporation device and this prevents penetration of water into the breathing air passages to the patient.

Accordingly it is an object of the invention to provide an improved breathing air humidifier for respirating devices which includes an evaporation surface in contact with the inspirated air on one side and with heated water on the other side and which is made of a material which impervious to water but pervious to water vapor so that the inspirated air is warmed and humidified during its passage through the foil surface.

A further object of the invention is to provide a breathing air humidifier for respirating devices which comprises an inspiration conduit which has a portion passing through a warmed water chamber and which includes a foil surface separating the inspiration air from the water in the chamber and which is made of a material which is impervious to water but pervious to water vapor.

A further object of the invention is to provide a humidifier which is simple in design, rugged in construction and economical to manufacture.

The various features of novelty which characterize the invention are pointed out with particularity in the claims annexed to and forming a part of this disclosure. For a better understanding of this invention, its operating advantages and specific objects attained by its uses, reference should be had to the accompanying drawings and descriptive matter in which there is illustrated a preferred embodiment of the invention.

GENERAL DESCRIPTION OF THE PREFERRED EMBODIMENT

Figure 1:
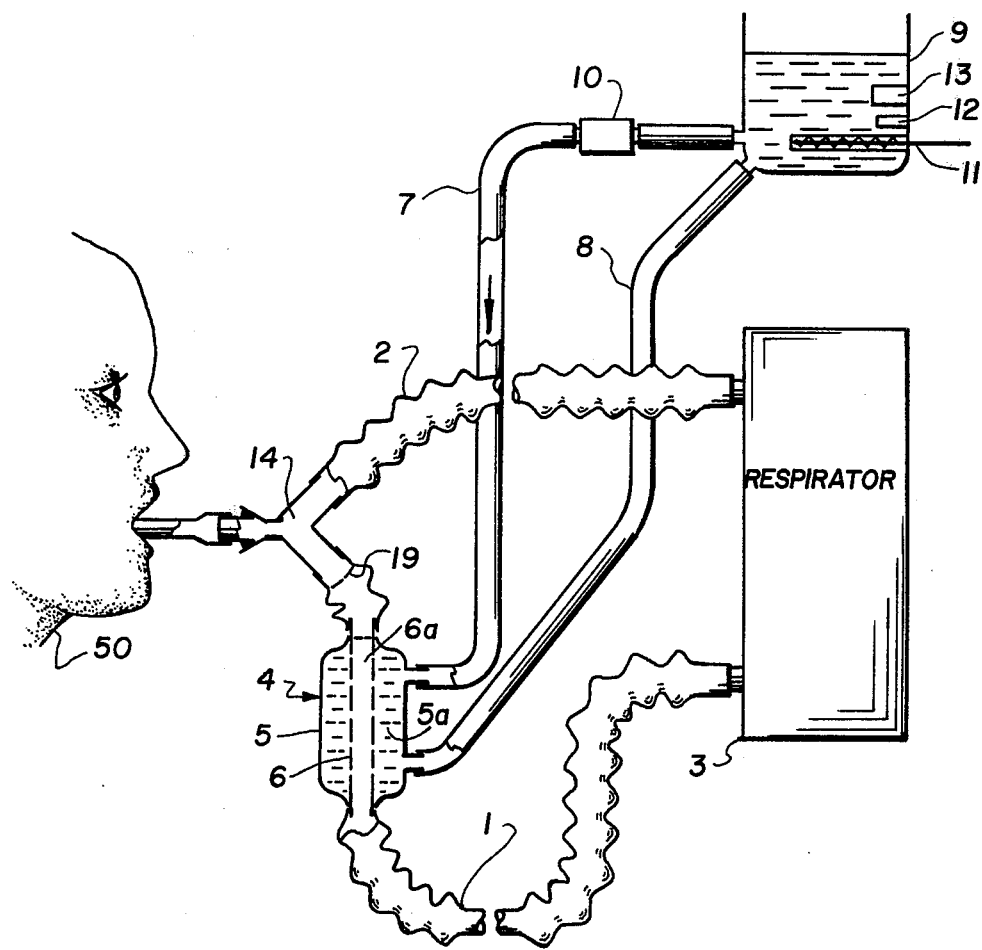
FIG. 1 is a diagrammatical illustration of a humidifier used with a respirator and constructed in accordance with the invention.
Figure 2:
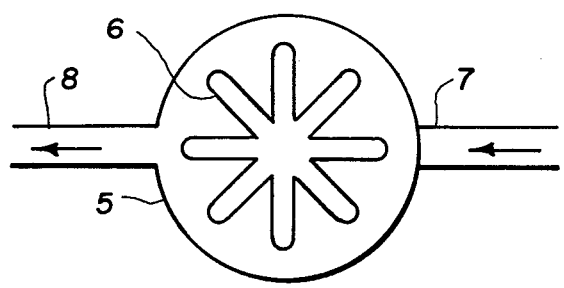
FIG. 2 is a partial horizontal sectional view of the humidifier shown in FIG. 1.

Referring to the drawings in particular the invention embodied therein as shown in FIGS. 1 and 2 comprises a respiration device which includes a respirator 3 which is connected to a patient 50 through an inspiration conduit 1 and an expiration conduit 2. A breathing air humidifier generally designated 4 is mounted in the inspiration conduit 1. The humidifier 4 comprises a receptacle 5 which defines an annular water chamber 5a which is separated from an interior passage 6a for the inspirated air by means of a foil material 6. The water chamber 5a is maintained filled with water which is heated for example by a heating element 11 disposed in a water supply tank 9 which is located above the humidifier 4. The supply tank includes a low water level alarm 13 which for example may be connected to a further supply of the liquid to keep it replenished and a thermostat 12 in the water maintains the operation of the heater 11 so that the water will be warmed before it is delivered through the water supply conduit 7 to the water chamber 5a. The water is circulated by a pump 10 and the water is returned to the supply tank through a return conduit 8. In the supply tank 9 the water is advantageously heated to a predetermined temperature preferably 36° C by means of the heating element 11 under the control of the thermostat 12.

In accordance with the invention the material of the foil 6 made such that it will be impervious to water but pervious to water vapor. The inspiration air stream which is fed through the inspiration conduit 1 flows past the inside of the foil surface 6 and entrains the water vapor which passes through the foil surface 6 and it is therefore humidified. Humidified air then passes to the patient through a Y-piece 14. The non-evaporated water circulates back into the supply tank 9 through the conduit 8. The water circuit is such that it insures that the water which flows through the humidifier will be at the proper temperature. The humidifier 4 may be placed closely upstream of the Y-piece and therefore in the immediate vicinity of the patient. A cooling down of the inspiration air and a corresponding condensation is thus prevented.

The mounting of the supply tank 9 above the humidifier 4 is preferable in order to insure that even at a maximum inspiration pressure of about 120 mm of water column that the water contacts the evaporation surface 6.

Figure 3:
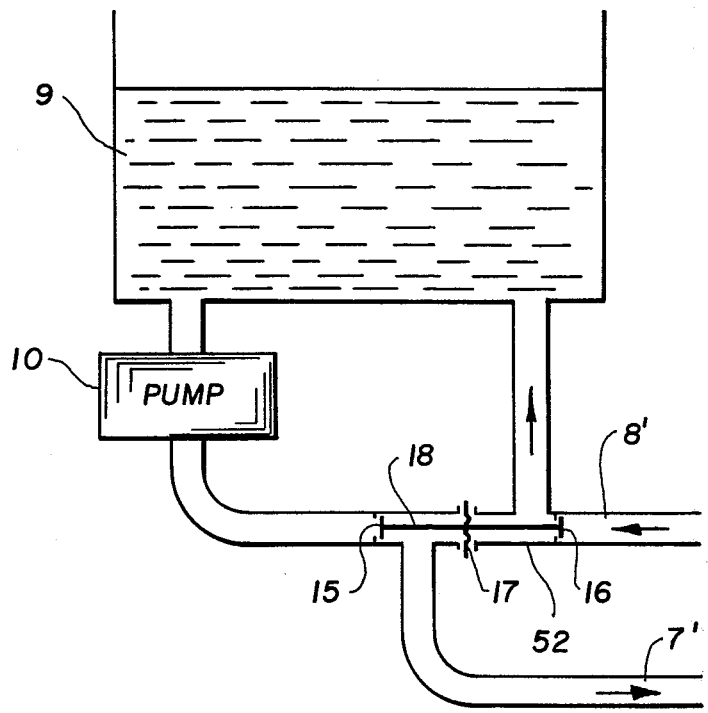
FIG. 3 is an enlarged detail view showing an alternate embodiment of water circulating connection for the humidifier shown in FIG. 1.

As shown in FIG. 2 foil surface 6 is advantageously of star shaped configuration to provide as large an engagement surface as possible and consequently an increased evaporation of the water and its entrainment by the inspirated air passing on the interior of the foil surface. Instead of using a static water pressure pressure on the evaporation surface 6 check valves may also be provided in the water supply and return conduits as shown in the embodiment of FIG. 3. In this arrangement check valves 15 and 16 are provided in a water supply conduit 7' and a water return conduit 8'. A diaphragm 17 is stretched across a connecting portion 52 between the conduits 7' and 8' and a coupling rod 18 interconnects the respective valves 15 and 16 and the diaphragm 17. Under inspiration pressure which is transmitted through the evaporation surface 6 into the water the check valves 15 and 16 will close and thereby interrupt the water circulation. In the expiration phase with the low pressure the valves 15 and 16 open again so that the breathing air humidifier 4 can again be supplied with warmed water. The pump 10 is made for pressure sufficiently low to avoid hindering of the operation of the check valves 15 and 16.

As shown in FIG. 1 an additional foil 19 may be located downstream of the evaporation surface 6 to provide a security device which would insure that no leakage which might occur through the evaporation surface 6 will be carried over to the patient.

While a specific embodiment of the invention has been shown and described in detail to illustrate the application of the principles of the invention, it will be understood that the invention may be embodied otherwise without departing from such principles.

What is claimed is:

1. A breathing air humidifier, comprising a respirator air supply conduit having a flexible tubular foil portion of a material impervious to water but pervious to water vapor, a receptacle surrounding said foil portion and defining an annular water chamber therearound, water reservoir means above said receptacle for circulating water to said water chamber, and a Y-piece having three interconnected tubular portions comprising a first tubular portion connectable to the mouth of the user, a second tubular portion connected to the said respirator air supply conduit downstream of said receptacle, and a third tubular portion having a respirator air return connection.

2. A breathing air humidifier according to claim 1, wherein the foil surface is made of a macroporous material which is hydrophobic.

3. A breathing air humidifier according to claim 1, wherein the foil surface is made of a microporous hydrophilic material.

4. A breathing air humidifier according to claim 1, including heating means for heating the water and causing its circulation from said supply tank to said water chamber.

5. A breathing air humidifier according to claim 1, wherein said means for supplying warm water to said water chamber comprises a pump.

6. A breathing air humidifier according to claim 1, wherein said means for supplying warm water to said water chamber includes pressure means for pressurizing the water so that it is maintained at a pressure greater than the maximum pressure occurring in the inspiration air stream.

7. A breathing air humidifier according to claim 1, wherein said foil surface comprises a member having a star shaped configuration, said inspiration air passing through the interior of said member.

8. A breathing air device according to claim 1, including means for producing a turbulence in the inspiration conduit adjacent said foil surface.

9. A breathing air humidifier according to claim 1, including second foil member extending across said inspiration conduit downstream of said humidifier and made of the same material as said foil surface and providing a safety barrier for insuring that no water is carried over to the patient.

10. A breathing air humidifier for respirator devices, comprising an inspiration conduit connectable to the user of the respirator having a portion with a foil surface of a material impervious to water but pervious to water vapor, means defining a water chamber directly adjacent at least one side of the foil surface and an inspiration air flow passage on the other side, and means for supplying warm water to the water chamber, said means for supplying warm water to said water chamber includes a supply tank, a water supply line leading from said tank to said water chamber, a water return line leading from said water chamber to said supply tank, a connection between said supply line and said return line having a diaphragm thereacross, a first valve located in said supply line, a second valve located in said return line, coupling means coupling said first and second valves in said supply and return lines to said diaphragm for opening or closing said valve simultaneously, said valves being controlled by pressure in the inspiration air stream acting through said foil surface into the water and adapted to move said diaphragm in a direction to interrupt the water circulation both in the water return conduit and the water supply conduit during the inspiration cycle.

* * * * *